(12) United States Patent
Panzner et al.

(10) Patent No.: US 7,312,206 B2
(45) Date of Patent: Dec. 25, 2007

(54) STEROL DERIVATIVES, LIPOSOMES COMPRISING STEROL DERIVATIVES AND METHOD FOR LOADING LIPOSOMES WITH ACTIVE SUBSTANCES

(75) Inventors: Steffen Panzner, Halle (DE); Gerold Endert, Halle (DE); Stefan Fankhänel, Halle (DE); Anja Behrens, Köln (DE)

(73) Assignee: Novosom AG, Halle (DE)

( * ) Notice: Subject to any disclaimer, the term of this patent is extended or adjusted under 35 U.S.C. 154(b) by 616 days.

(21) Appl. No.: 10/468,652

(22) PCT Filed: Feb. 21, 2002

(86) PCT No.: PCT/EP02/01879

§ 371 (c)(1), (2), (4) Date: Feb. 11, 2004

(87) PCT Pub. No.: WO02/066490

PCT Pub. Date: Aug. 29, 2002

(65) Prior Publication Data

US 2004/0131666 A1  Jul. 8, 2004

(30) Foreign Application Priority Data

Feb. 21, 2001  (DE) ............... 101 09 898

(51) Int. Cl.
  *A61K 31/58* (2006.01)
  *A61K 9/127* (2006.01)
  *C07J 43/00* (2006.01)
  *C12N 15/00* (2006.01)

(52) U.S. Cl. .............. 514/176; 540/107; 540/108; 540/113; 514/176; 435/320.1; 424/450

(58) Field of Classification Search .......... 514/176; 552/107, 108, 113; 435/320.1; 424/450
See application file for complete search history.

(56) References Cited

U.S. PATENT DOCUMENTS

| 4,788,182 A | 11/1988 | Baschang et al. |
| 4,891,208 A | 1/1990 | Janoff et al. |
| 5,365,487 A | 11/1994 | Patel et al. |
| 5,888,821 A | 3/1999 | Reszka |
| 2003/0157181 A1 | 8/2003 | Panzner et al. |

FOREIGN PATENT DOCUMENTS

| EP | 0169812 | 1/1986 |
| JP | 02331417 | 11/1990 |
| WO | WO 93/05162 | 3/1993 |
| WO | WO 96/20208 | 7/1996 |
| WO | WO 97/39019 | 4/1997 |
| WO | WO 97/31935 | 9/1997 |
| WO | WO 97/454442 | 12/1997 |
| WO | WO 00/28972 | 3/2000 |
| WO | WO 01/64330 A1 | 3/2001 |
| WO | WO 02/00680 | 1/2002 |

OTHER PUBLICATIONS

Budker et al:, *PH-Sensitive, Cationic Liposomes: A New Synthetic Virus-Like Vector*, Bio/Technology, Nature Publishing Co., New York, NY, US; vol. 14, Jun. 1996.

Tang F. et al.; *Introduction of a Disulfide Bond Into a Cationic Lipid Enhances Transgene Expression of Plasmid DNA*; Biochemical and Biophysical Research Communications, Academic Press Inc., Orlando, FL, US; vol. 242, No. 1; Jan. 6, 1998.

Fichert T et al; *Synthesis and Transfection Properties of Novel Non-Toxic Monocationic Lipids. Variation of Lipid Anchor, Spacer and Head Group Structure*, Bioorganic & Medicinal Chemistry Letters, Oxford, GB; vol. 10, No. 8, Apr. 2000.

Tachibana et al, *Intracellular Regulation of Macromolecules Using pH-Sensitive Liposomes and Nuclear Localization Signal: Qualitative and Quantitative Evaluation of Intracellular Trafficking*, Biochemical and Biophysical Research Communications 251, 538-544 (1998) Article No. TC989460.

*Handbook of Chemistry and Physics*, 73. Band, S. 8-37 ff date needed.

T.V. Konstantinova et al., *Synthesis of Cholesterol-Containing Cationic Amphiphiles with Heterocyclic Bases*, Russian Journal of Bioorganic Chemistry, XP002207246.

*Primary Examiner*—Barbara P. Badio
(74) *Attorney, Agent, or Firm*—Akerman Senterfitt; Stephan Pendorf

(57) ABSTRACT

Disclosed is a sterol derivative having a pKa value of 3.5-8 according to the general formula cation-spacer 2-Y-spacer 1-X-sterol, wherein Y and X represent bonding groups. The invention also relates to liposomes containing said sterol derivatives.

22 Claims, 2 Drawing Sheets

Figure 1:
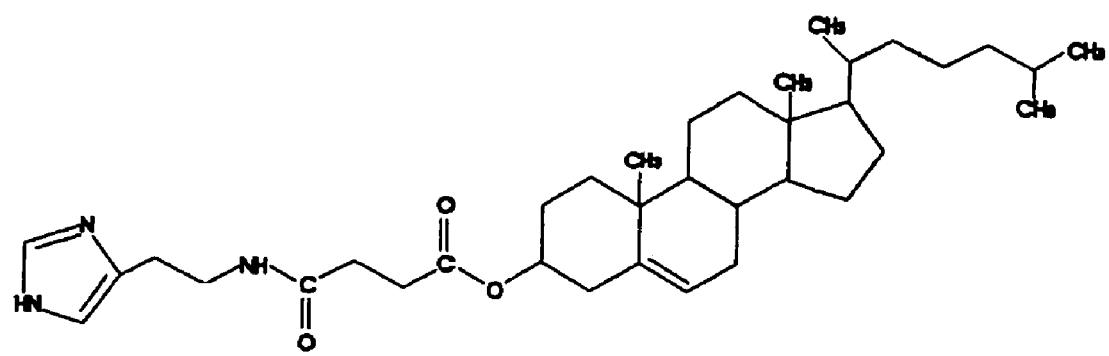
Figure 1:
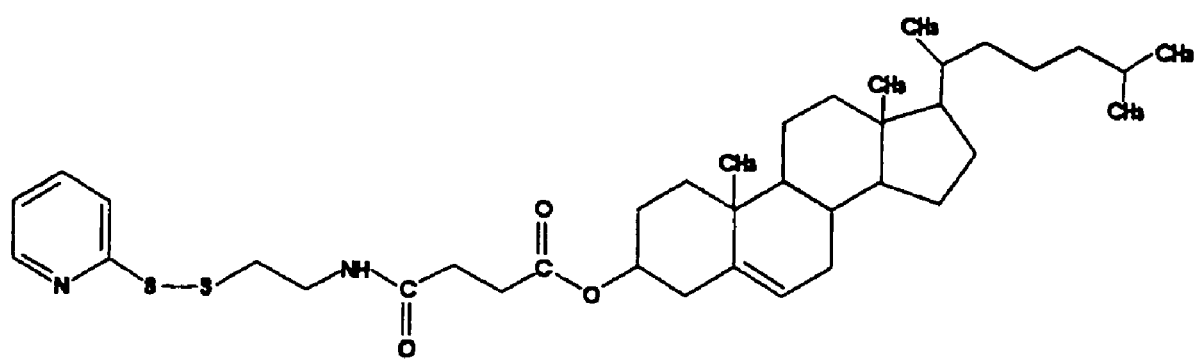

A.

B.

A.

B.

STEROL DERIVATIVES, LIPOSOMES COMPRISING STEROL DERIVATIVES AND METHOD FOR LOADING LIPOSOMES WITH ACTIVE SUBSTANCES

CROSS REFERENCE TO RELATED APPLICATIONS

This application is a national stage of PCT/EP02/01879 filed Feb. 21, 2002. Priority is claimed from German Patent Application No. 101 09 898.7 filed Feb. 21, 2001.

FIELD OF THE INVENTION

The invention relates to polar compounds based on a sterol skeleton, the 3-position of the ring system being substituted by an organic cation having a pK value of between 3.5 and 8. The invention also relates to liposomes containing such compounds.

BACKGROUND OF THE INVENTION

The term "lipids" summarizes three classes of natural materials which can be isolated from biological membranes: phospholipids, sphingolipids, and cholesterol, including its derivatives.

These substances are of technical interest in the production of liposomes. Inter alia, such liposomes can be used as containers for active substances in pharmaceutical preparations. In such uses, efficient and stable packaging of the cargo and controllable release of the contents are desirable. Both of these requirements are not easy to combine: the more stable and compact the packaging, the more difficult the release of the entrapped active substance therefrom. For this reason, liposomes changing their properties in response to an external stimulus have been developed. Thermosensitive and pH-sensitive liposomes are well-known. The pH-sensitive liposomes are of special interest, because this parameter undergoes changes even under physiological conditions, e.g. during endocytotic reception of a liposome in a cell, or during passage of the gastrointestinal tract.

The following abbreviations will be used hereinafter:
CHEMS Cholesterol hemisuccinate
PC Phosphatidyl choline

| | |
|---|---|
| PE | Phosphatidyl ethanolamine |
| PS | Phosphatidyl serine |
| His-Chol | Histaminylethaneamine-cholesterol hemisuccinate |
| Py-Chol | Pyridylethaneamine-cholesterol hemisuccinate |
| Mo-Chol | Morpholinoethaneamine-cholesterol hemisuccinate |
| PDEA-Chol | Pyridyldithioethaneamino-cholesterol hemisuccinate |

According to the prior art, pH-sensitive liposomes particularly comprise CHEMS. CHEMS, in mixture with phosphatidyl ethanolamine, is used to produce pH-sensitive liposomes (Tachibana et al. (1998); BBRC 251, 538-544, U.S. Pat. No. 4,891,208). Such liposomes can enter cells by endocytosis and are capable of transporting cargo molecules into the interior of cells on this route, without doing damage to the integrity of the cellular membrane.

One substantial drawback of CHEMS is its anionic character. Liposomes produced using same have a negative overall charge and, disadvantageously, are taken up by cells with low efficiency. Despite the transfer mechanism described above, they are barely suitable for the transport of macromolecules into cells.

For this purpose, the art uses cationic liposomes having a preferably high and constant surface charge. The positive overall charge of such particles leads to electrostatic adherence to cells and subsequently to efficient transport into same. The use of these compounds and of liposomes produced using same remains restricted to in vitro or ex vivo applications, because such positively charged liposomes disadvantageously result in uncontrolled formation of aggregates with serum components.

SUMMARY OF THE INVENTION

The object was therefore to produce new compounds,
i) by means of which active substances can be entrapped in liposomes and released therefrom when changing the pH value; and
ii) the presence of which aids to achieve the production of cationic liposomes which can be mixed with serum without formation of larger aggregates.

Other objects of the invention involve finding ways allowing easy and low-cost production of the desired compounds and incorporation thereof in high amounts in liposomal membranes.

The object of the invention is accomplished by means of a sterol derivative with a pKa value of between 3.5 and 8, according to the general formula:

Cation-Spacer 2-Y-Spacer 1-X-Sterol, wherein Y and X represent linking groups. Depending on the cation used, compounds are obtained which undergo changes in their charge at a specific pH value owing to the sterol component and allow incorporation thereof in liposomal membranes in high amounts. Ordinary and inexpensive sterols or derivatives thereof can be used as starting compounds. Accordingly, the object of the invention can be accomplished by conjugating pH-sensitive cations to the 3-position of a sterol skeleton.

Among the membrane-forming or membrane-bound groups of a biological bilayer membrane, the sterols are of special interest because these compounds are available at low cost, involve ordinary chemistry, and allow incorporation in membranes in high amounts without increasing the permeability thereof or even completely destroying their membrane character. However, in order to retain this latter feature, it is important that substitution with a polar molecule be at the 3-position of the sterol.

The cation or cationic group can be e.g. a nitrogen base. The sterol is cholesterol, for example. Situated between the cationic group and the sterol skeleton are the molecule fragments spacer 2-Y-spacer 1-X.

For example, spacer 1 is a lower alkyl residue of linear structure, which has 8 C atoms and includes e.g. 2 ethylenically unsaturated bonds. Spacer 2 is e.g. a lower alkyl residue of linear structure, which may have 8 C atoms and includes 2 ethylenically unsaturated bonds.

The overall molecule assumes its pH-dependent charge characteristics by one or more organic cations with a pKa value between 3.5 and 8. Typical molecules or molecule fragments with this property are nitrogen bases. These nitrogen bases are linked to the 3-position of the sterol skeleton via spacers and coupling groups, thus forming a compound according to the formula of the invention. In many cases, e.g. where the nitrogen bases are in the form of a ring system, positional isomers are existing, wherein the linking spacer is substituted to various positions of the organic cation. Such positional isomers fall within the disclosure of this invention. In many cases, the pKa values of the organic cation can be influenced via said positional isomerism alone. The relevant fundamental rules are well-known to those skilled in the art. Alternatively, these effects can be estimated from tabular compilations (*Handbook of Chemistry and Physics*, Vol. 73, pp. 8-37ff.).

BRIEF DESCRIPTION OF THE FIGS.

FIG. 1 A. Structural formula of Histidineamido-cholesterol hemisuccinate, m.w. 580 g/mol; B. structural formula of Pyridyldithioethaneamido-cholesterol hemisuccinate, m.w. 655 g/mol.

Figure 2:
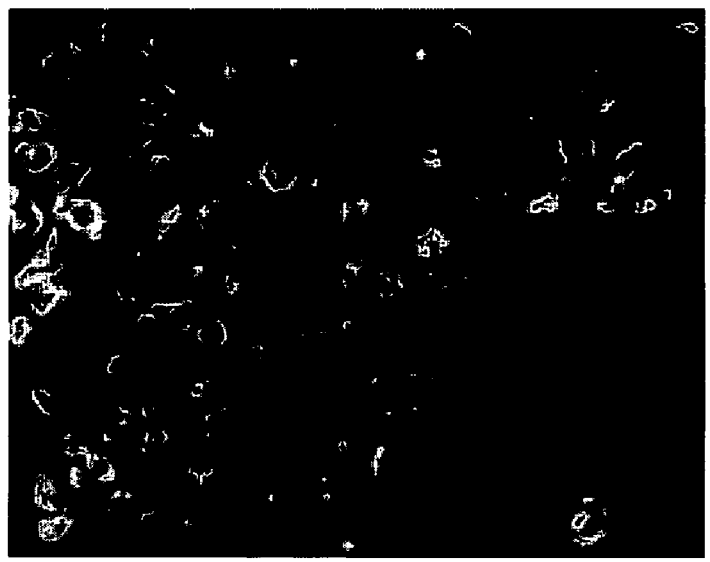
Figure 2:
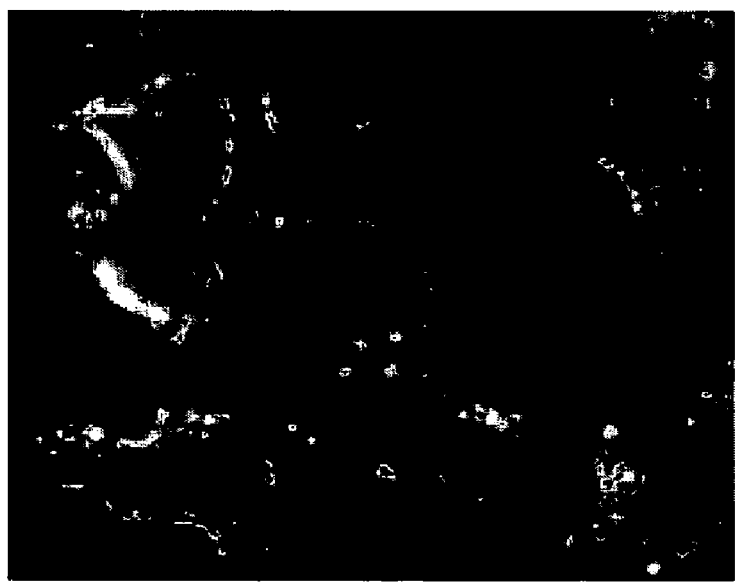

FIG. 2 Shows transfection of HeLa cells according to Example 12: A. Transfection by TRITC dextran with liposomes (DOPE 60/His-Chol 40); B. Transfection by TRITC dextran with liposomes (POPC 60/His-Chol 40).

DETAILED DESCRIPTION

In a preferred embodiment of the invention, the sterol derivative has a pKa value of between 4 and 6.5. Advantageously, this pKa value falls in a range which is of crucial importance for the physiology of numerous organisms.

In another preferred embodiment of the invention, the cations are nitrogen bases. The cations preferably can be derived from piperazines, imidazoles, morpholines, purines and/or pyrimidines.

Coupling reactions result in amphiphilic organic cations, e.g. those derived from the following classes of substances: o-, m-, p-anilines; 2-, 3- or 4-substituted anisidines, toluidines or phenetidines; 2-, 3-, 5-, 6-, 7- or 8-substituted benzimidazoles, 2-, 3-, 4- or 5-substituted imidazoles, 1- or 5-substituted isoquinolines, 2-, 3- or 4-substituted morpholines, 2-, 3- or 4-substituted picolines, 1-, 2- or 3-substituted piperazines, 2-, 5- or 6-modified pterines, 3-, 4-, 5-, 6- or 9-substituted purines, 2- or 3-substituted pyrazines, 3- or 4-substituted pyridazines, 2-, 3- or 4-modified pyridines, 2-, 4-, 5- or 6-substituted pyrimidines, 1-, 2-, 3-, 4-, 5-, 6- or 8-substituted quinolines, 2-, 4- or 5-substituted thiazoles, 2-, 4- or 6-substituted triazines, or derivatives of tyrosine. Particularly preferred are piperazines, imidazoles, morpholines, purines and/or pyrimidines.

Highly preferred are molecule fragments such as occurring in biological systems, i.e., for example: 4-imidazoles (histamines), 2-, 6- or 9-purines (adenines, guanines, adenosines, or guanosines), 1-, 2- or 4-pyrimidines (uracils, thymines, cytosines, uridines, thymidines, cytidines), or pyridine-3-carboxylic acids (nicotinic esters or amides).

The above-mentioned structural fragments may also have additional substituents. For example, these can be methyl, ethyl, propyl, or isopropyl residues, more preferably in hydroxylated form, including one or two hydroxyl groups. Also, these can be hydroxyl or keto functions in the ring system. In addition, other structural fragments are also possible unless anionically dissociated molecule portions are formed in a pH range between 3.5 and 8.5, e.g. carboxylic acids, sulfonic acids, or some aromatic hydroxyl groups or enols.

Nitrogen bases with preferred pKa values are also formed by single or multiple substitution of the nitrogen atom with lower alkanehydroxyls such as hydroxymethyl or hydroxyethyl groups. Suitable organic bases from this group are e.g. aminopropanediols, triethanolamines, tris(hydroxymethyl) methylamines, bis(hydroxymethyl)methylamines, tris(hydroxyethyl)methylamines, bis(hydroxyethyl)methylamines, or the corresponding substituted ethylamines. Coupling of these fragments to the hydrophobic portion of the molecule may proceed either via the nitrogen of the base or via any of the hydroxyl functions.

In addition to sterol derivatives including a single organic cation, those including two or three identical or different groups are also preferred. All of these groups are required to have a pKa value in the above-mentioned range. One suitable complex group is the amide of histamine and histidine or of histamine and histidylhistidine.

Anionic groups such as carboxylic acids, sulfonic acids, enols, or aromatic hydroxyls are allowable as component of the molecule only if undissociated in the claimed pH range between 3.5 and 8.5. In general, this is the case if the pKa value is above 9.5.

In another preferred embodiment of the invention, the linking group X has the structure —(C=O)—O—; —(C=O)—NH—; —(C=O)—S—; —O—; —NH—; —S—; or —CH=N—, for example. In particular, the linking group Y corresponds in its structure to the group X, and may additionally assume the structure —O—(O=C)—; —S—(O=C)—; —NH—(O=C)—; or —N=CH—. The Y group can be omitted in those cases where the organic cation can be coupled directly to the sterol skeleton, e.g. in the esterification of 4-imidazoleacetic acid with cholesterol.

In another preferred embodiment of the invention, spacer 1 is a lower alkyl residue of linear, branched or cyclic structure, which has from 1 to 8 C atoms and includes 0, 1 or 2 ethylenically unsaturated bonds. Spacer 1 may have hydroxyl groups so as to increase the polarity of the molecule. In particular, spacer 1 can be a sugar. Spacer 2 is a lower alkyl residue of linear, branched or cyclic structure, which has from 0 to 8 C atoms and includes 0, 1 or 2 ethylenically unsaturated bonds. Spacer 2 may have hydroxyl groups so as to increase the polarity of the molecule. In particular, spacer 2 can be a sugar.

Methods of performing such coupling reactions are well-known to those skilled in the art and may vary depending on the starting material and coupling component employed. Typical reactions are esterification, amidation, addition of amines to double bonds, etherification, or reductive amination.

A particularly preferred method of coupling is amidation of sterol hemisuccinates. Inter alia, molecules satisfying the requirements according to the object of the invention can be produced by coupling of histamine, N-(2-aminoethyl)morpholine, N-(2-aminoethyl)piperazine, N-(2-aminoethyl)pyridine, or pyridyldithioethenylamine. The compounds thus obtained will be referred to as His-Chol, Mo-Chol, Pip-Chol, Py-Chol, or PDEA-Chol herein.

In another preferred embodiment of the invention, the sterols are particularly cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en-3β-ol, 7-hydroxycholesterol, epicholesterol, ergosterol, and/or dehydroergosterol, as well as other related compounds.

The sterols that are used may bear various groups in the 3-position thereof, which groups allow for ready and stable coupling or optionally assume the function of a spacer. Particularly suitable for direct coupling are the hydroxyl group which is naturally present, but also, the chlorine of sterol chlorides, or e.g. the amino group of sterolamines, or the thiol group of thiocholesterol.

The invention also relates to liposomes comprising the substances according to the invention. All of the substances or compounds of the invention can be incorporated in high amounts in liposomal membranes, resulting in a positive charge of the overall particle only if the pH value of the medium is smaller than (pKa+1) of the compounds according to the invention.

In a special embodiment of the invention, the amount of sterol derivative is 50 mole-% at maximum. Compositions including at least 5 mole-% of compound, but 40 mole-% at maximum, are particularly preferred. Compositions including at least 10 mole-% of sterol derivative and 30 mole-% at maximum are highly preferred.

Another embodiment wherein the liposomes specifically comprise phosphatidyl choline, phosphatidyl ethanolamine and/or diacylglycerol is also convenient. Cholesterols themselves are incapable of forming liposomes, and therefore, addition of further lipid is necessary. In particular, this lipid can be a phospholipid. Obviously, further modifications of the liposome are possible. Thus, the use of polyethylene glycol-modified phospholipids or analogous products is particularly advantageous.

In another embodiment of the invention, the liposomes have an average size of between 50 and 1000 nm, preferably between 50 and 300 nm, and more preferably between 60 and 130 nm.

In another preferred embodiment, the liposomes comprise active substances. For example, the liposomes according to the invention are suitable for parenteral application. They can be used e.g. in cancer therapy and in the therapy of severe infections. To this end, liposome dispersions can be injected, infused or implanted. Thereafter, they are distributed in the blood or lymph or release their active substance in a controlled fashion as a depot. The latter can be achieved by highly concentrated dispersions in the form of gels. The liposomes can also be used for topical application on the skin. In particular, they may contribute to improved penetration of various active substances into the skin or even passage through the skin and into the body. Furthermore, the liposomes can also be used in gene transfer. Due to its size and charge, genetic material is usually incapable of entering cells without an aid. For this purpose, suitable carriers such as liposomes or lipid complexes are required which, together with the DNA, are to be taken up by the respective cells in an efficient and well-directed fashion. To this end, cell-inherent transport mechanisms such as endocytosis are used. Obviously, the liposomes of the invention can also be used as model membranes. In their principal structure, liposomes are highly similar to cell membranes. Therefore, they can be used as membrane models to quantify the permeation rate of active substances through membranes or the membrane binding of active substances.

Advantageously, liposomes produced using the substances of the invention show low non-specific binding to cell surfaces. It is this low non-specific binding which is an essential precondition for achieving specific binding to target cells. Target control of the vehicles is obtained when providing the above-described liposomes with additional ligands. As a result, the active substance can be accumulated specifically in such cells or tissues which exhibit a pathological condition.

One important use of the substances according to the invention is therefore in the construction of vectors for transfer of active substances in living organisms. The vectors are particularly suited for the transport of therapeutic macromolecules such as proteins or DNA which themselves are incapable of penetrating the cell membrane or undergo rapid degradation in the bloodstream.

Advantageously, antibodies, lectins, hormones or other active substances can be coupled to the surface of liposomes under mild conditions in high yields. In one variant of the teaching according to the invention, the liposomes for such a use comprise a sufficient amount of PDEA-Chol in addition to other lipids, including those mentioned in the present specification. The amount of PDEA-Chol employed will depend on the desired use. Thus, liposomes loaded with a marker require a high ratio of this signal generator to the component determining the specificity. In this case, only a low number of antibodies per liposome have to be coupled.

In a preferred embodiment of the invention, the liposomes comprise a protein, a peptide, a DNA, an RNA, an antisense nucleotide, and/or a decoy nucleotide as active substance.

In a particularly preferred embodiment of the invention, at least 80% of the active substance is inside the liposome.

The invention also relates to a method of loading liposomes with active substances, wherein one defined pH value is used for encapsulation, and a second pH value is adjusted to remove unbound active substance.

The invention also relates to a method of loading liposomes with active substances, wherein the liposomes are made permeable at a well-defined pH value and sealed.

The invention also relates to the use of the liposomes in the production of nanocapsules.

The invention also relates to the use of the liposomes in the production of release systems in diagnostics.

Advantageously, the liposomes are used for the transport and/or release of active substances.

In another embodiment, the liposomes conveniently are used as depot formulation and/or as circulative depot.

Advantageously, the liposomes can be used in intravenous or peritoneal application.

In another embodiment of the invention, the liposomes are used with advantage as vector to transfect cells in vivo, in vitro and ex vivo.

Surprisingly, it has been determined that the permeability of the lipid layer of the inventive liposomes particularly depends on the pH value and thus, on the state of charge of the sterol derivative. In addition, when using the well-known CHEMS, an increase in permeability occurs only in the simultaneous presence of high amounts of phosphatidyl ethanolamine (PE) in the membrane. This phospholipid does not form membranes by itself, being stabilized artificially by CHEMS. However, one drawback of such liposomes is their low stability which can be seen in the fact that smaller molecules of active substance slowly diffuse out even without a change in pH.

When using His-Chol, in particular, the membranes comprised of phosphatidyl choline (PC) are made permeable in such a way that entrapped active substances or markers will diffuse out within minutes to hours. However, these membranes themselves are stable, showing low initial permeability. Liposomes using the structures according to the invention are therefore suited to construct release systems wherein release of active substances is to proceed in dependence on the pH value of the medium.

Surprisingly, it has also been found that amounts of proteins or DNA above average can be enclosed in liposomes including the compounds described herein in the membranes thereof. The efficiency of such incorporation depends on the pH value of the solution employed. Therefore, a process for efficient encapsulation of proteins or DNA in liposomes can be performed by initially adjusting a pH value that would result in good binding of the cargo molecules to the liposomes. With DNA as polyanion, low pH values of about 4 to 5 are used. With proteins, a useful pH value will depend on the isoelectric point of the protein, which should be below the pKa value of the substance according to the invention. Encapsulation is particularly effective when the pH value of the medium is selected so as to range between the isoelectric point of the protein and the pKa value of the sterol derivative. The proteins then will have a negative charge, while the lipid layer already has a positive net charge. If necessary, non-incorporated cargo molecules adhering on the outside can be removed by simply increasing the pH value. This step is necessary in all those cases where non-incorporated cargo molecules would give rise to aggregation of the liposomes. One advantageous fact when using the components of the invention is that the entrapped active substances must be maintained under conditions allowing interaction with the lipid layer only during the period of actual enclosure. Once the lipid layer remains closed in itself, it is possible to change to other conditions. Thereby, possible inactivation of active substances, particularly of proteins, can be minimized.

Liposomes comprising the components of the invention can be coated with polymers under conditions well-known to those skilled in the art, where single or multiple deposition of such substances on the surface is possible, in particular. In multiple deposition, optionally in the presence of crosslinkers, liposomal nanocapsules are formed as described in WO 00/28972 or WO 01/64330.

One advantageous fact when using the substances described herein is that the electrostatic interaction with the polyelectrolyte can be interrupted. As is well-known, the interaction of a polyelectrolyte with charge carriers of the liposomal membrane may give rise to demixing of membrane components and formation of lipid clusters. In many cases, such demixing is accompanied by a permeabilization of the liposomes. The substances of the invention allow for elimination of this interaction following the coating process. When increasing the pH value at this point, the liposomes will be entrapped in the nanocapsules merely in a steric fashion, and interaction between the membrane and polyelectrolytes does no longer exist. In this way, cluster formation of lipids and associated permeabilization of the membrane can be circumvented.

In one variant of the teaching according to the invention, these changes in permeability are used in a well-directed fashion in loading liposomes. To this end, an active substance to be enclosed can be added to a medium under conditions of high permeability, followed by adjusting conditions of low permeability. In this way, the active substance will remain inside the liposomes. Thereafter, non-entrapped active substance can be removed, if necessary. Such changes in permeability can be induced on liposomes or on liposomal nanocapsules.

Surprisingly, it has also been found that liposomes including e.g. His-Chol or Pip-Chol in the membranes thereof are capable of chelating metal ions. This property results in an increase of the positive charge of the liposome. This effect is observed to be particularly strong at neutral pH values, because the inherent charge of the compound is low in this case. Owing to their chelating properties, such liposomes can be used in biochemical diagnostics and in pharmaceutical therapy.

In a detection system, such liposomes can be loaded with metal ions whose fluorescence is enhanced by chelate formation, i.e., terbium or europium ions, for example. Liposomes for such uses additionally include components determining the specificity, i.e., antibodies, lectins, selecting, receptors, or hormones, or RNA aptamers. In a particularly preferred embodiment of the use according to the invention, the presence of these metal ions is restricted to the volume of the liposomes so as to avoid non-specific signals from slowly released metal ions adhering on the outside.

Coupling of pyridyldithioethenylamine to CHEMS provides a compound with a special combination of desirable properties. The terminal pyridyl group results in significant positive charging of the membrane even under mild conditions (pH 6 to 7). Liposomes produced using this compound are capable of binding proteins or nucleic acids in large amounts above average. By reducing the disulfide bond, e.g. using dithiothreitol or tris(2-carboxyethyl)phosphine, a free thiol function is generated, resulting in neutralization of the surface. Under these conditions, such enhanced binding of proteins or nucleic acids is decreased. Ultimately, it is completely lost when increasing the pH value, because the formation of thiolate ions results in a negatively charged surface.

In those cases where biological macromolecules possess thiol functions of their own, binding thereof can be retained. This is the case with numerous proteins. Where other materials are concerned, a person skilled in the art will be familiar with procedures of introducing free thiol functions in such molecules, while retaining the biological activity thereof (G. Hermanson, Bioconjugate Techniques). Substances including a free thiol function can be fixed covalently to the surface of such lipid layers by means of a disulfide exchange reaction.

Owing to their particularly favorable properties in binding and coupling of proteins, liposomes including PDEA-Chol are especially suitable in the production of nanocapsules on liposomal templates such as described in WO 00/28972.

Surprisingly, it has also been found that liposomes including PDEA-Chol are capable of changing their permeability in accordance with the redox state. Reductive removal of the pyridyl group results in permeabilization of the membrane.

Surprisingly, it has also been found that the liposomes according to the invention readily undergo fusion with other membranes at low pH values. In general, this step requires the presence of a larger amount of PE in the membrane. As a result of its tendency of forming hexagonal phases, said PE assumes the function of a helper lipid. However, the inferior stability of such membranes is disadvantageous, and gradual release of entrapped active substances is frequently observed.

However, liposomes produced using the substances according to the invention undergo effective fusion even in the absence of such a helper lipid. Thus, when using the substances of the invention, it is possible to produce liposomes which are capable of stably encapsulating an active substance, but undergo fusion with cell membranes under the conditions of low pH values to release the active substance there.

This combination of two properties is an important precondition for the incorporation of cargo molecules in cells. In fusion of liposomes with cell envelopes or components, the aqueous volumes of both partners combine, with no opening of the membrane structures to the medium taking place. As a result, uncontrolled influx or efflux of other substances is avoided.

One essential precondition for the use of liposomes for experimental or therapeutic purposes is their compatibility with cells and tissues. A number of well-known compounds used to incorporate DNA or proteins in cells (for example, the cationic lipid DOTAP) are cytotoxic.

Surprisingly, it has also been found that the compounds of the invention exhibit reduced cytotoxicity. These measurements will be illustrated in the experimental section. Thus, compared to the commonly used DOTAP, His-Chol shows lesser toxic effects in the MTT test.

Another precondition for the construction of vectors to be used in gene or protein transport into cells is their compatibility with serum or blood. Due to their strong cationic charge, vectors known at present form uncontrollable large aggregates, resulting in formation of thrombi in the organism. Their use in vivo is therefore practically impossible and is restricted to in vitro or ex vivo applications.

Surprisingly, it has been found that liposomes constructed using the components of the invention do not form any aggregates in serum or blood.

Another precondition for the construction of vectors to be used in protein or gene transfer is their stability under physiological conditions. Upon application into the blood circulation, liposomes are attacked by components of the complement system and undergo rapid lysis. This reaction proceeds within minutes. As a result, pores are formed in the membrane, which allow even large molecules such as proteins to diffuse out therethrough. At present, stabilization of liposomes with respect to this mechanism is only possible by incorporating cholesterol in the lipid layer. While such liposomes are highly stable, they are no longer able to interact with cells or readily release their active substance. Surprisingly, it has been found that liposomes constructed using the components of the invention are stable in serum or blood for several hours. Even under such conditions, the release of active substance is low.

A liposomal vector for the transport of active substances must satisfy at least three preconditions: it must have low toxicity, entrap the active substance firmly and stably, and be compatible with serum or blood.

All of these three preconditions are satisfied by liposomes produced using the substances according to the invention. The liposomes disclosed herein are therefore well suited for therapeutic uses. Other properties supporting such uses are good loadability with active substances and well-directed release of these substances by permeabilization of the membrane at suitable pH values or redox states.

Without intending to be limiting, the invention will be explained in more detail with reference to the following examples.

EXAMPLE 1

Synthesis of His-Chol 1.31 g of cholesterol hemisuccinate is dissolved in 20 ml of DMF at room temperature. The solution is added with 438 mg of carbonyldiimidazole dissolved in 20 ml of DMF. The mixture is allowed to stir for 1 hour and subsequently added with 300 mg of histamine. The mixture is stirred overnight and concentrated thoroughly in vacuum. The residue is purified by column chromatography on silica (Kieselgel 60), with chloroform/methanol 10:1 being used as eluant. (Yield 54%; 1.45 mmol), pure in HPLC, identity determined using MS and $^{13}$C-NMR.

EXAMPLE 2

Synthesis of PDEA-Chol

The procedure for the synthesis of PDEA-Chol is as above. Instead of histamine, 600 mg of pyridyldithioethaneamine hydrochloride is used.

EXAMPLE 3

Synthesis of Mo-Chol

The procedure for the synthesis of Mo-Chol is as above. Instead of histamine, 350 mg of 4-(2-aminoethyl)morpholine is used.

EXAMPLE 4

Preparation of Cationic pH-Sensitive Liposomes 5 mg of His-Chol and 9.8 mg of POPC are dissolved in 4 ml of chloroform/methanol (1:1 v/v) and dried completely in a rotary evaporator. The lipid film is hydrated with 4.3 ml of a corresponding buffer (10 mM Kac, 10 mM HEPES, 150 mM NaCl, pH 7.5) at a lipid concentration of 5 mM using brief ultrasonic treatment (5 minutes). Finally, the suspension is frozen and, following thawing, subjected to multiple extrusions (Avestine LiposoFast, polycarbonate filter, pore width 200 nm).

The profile of the zeta potential at various pH values is illustrated in the Table below.

| pH value | Zeta potential in mV |
|---|---|
| 4.4 | +52 |
| 6.2 | −3 |
| 7.5 | −13 |

EXAMPLE 5

Permeability

Liposomes are produced generally as in Example 4. The following lipid mixtures are used (figures in mole-%)

| | |
|---|---|
| A: DPPC 60 | His-Chol 40 |
| B: DPPC 60 | CHEMS 40 |
| C: POPC 60 | His-Chol 40 |
| D: POPC 60 | CHEMS 40 |

The lipids are dissolved in the solvent mixture as indicated and dried under vacuum. The lipid films are hydrated with 100 mM carboxyfluoresceine, 50 mM NaCl, pH 7.5, at a lipid concentration of 15 mM and frozen, thawed and extruded as above. Non-entrapped carboxyfluoresceine is removed by gel filtration.

20 μl of the liposomes thus obtained are incubated with 2 ml of buffer (10 mM potassium acetate, 10 mM HEPES). After 90 min, the amount of discharged carboxyfluoresceine is determined by measuring the fluorescence intensity of the sample. A comparative sample with complete release of the entrapped marker is obtained by addition of 0.2% Triton X-100 to the batch.

| | A | B | C | D |
|---|---|---|---|---|
| pH 4.4 | 8 | 38 | 80 | 39 |
| pH 5.4 | 7 | 7 | 35 | 18 |
| pH 6.4 | 6 | 9 | 18 | 16 |
| pH 7.4 | 7 | 7 | 17 | 15 |
| pH 8.4 | 5 | 11 | 15 | 15 |

EXAMPLE 6

Chelating of Metal Ions

Liposomes are produced as in Example 4. 40 µl of these liposomes are suspended in 7 ml of buffer (10 mM potassium acetate, 10 mM HEPES, pH 4.2 or pH 7.5). Subsequently, the metal ions are added with the concentrations as indicated, and the zeta potential of the liposomes is measured.

| Ions | pH 4.2 | pH 7.5 |
| --- | --- | --- |
| $Ni^{2+}$ 10 mM | +16.8 | 11.6 |
| $Ca^{2+}$ 10 mM | +40.5 | +4.6 |
| $Zn^{2+}$ 10 mM | +65.4 | not measurable |
| No addition | +47.6 | +2.4 |

At neutral pH, chelating of nickel ions is clearly detectable. At slightly acidic pH, nickel ions are not bound anymore, but zinc ions are. The non-transition metal calcium behaves indifferently, forming no chelate complexes.

EXAMPLE 7

Binding of DNA 1 mg of DNA (herring sperm, SIGMA D3159) is dissolved in 1 ml of water. Using the liposomes from Example 4, a 0.2 mM suspension in buffer (10 mM potassium acetate, 10 mM HEPES, pH 4.2 or pH 7.5) is produced. 45 µl of DNA solution each time is added to 1 ml of these different liposome samples and mixed rapidly. After 15 minutes of incubation, the sample is filled up with 6 ml of the corresponding buffer, and the zeta potential of the liposomes is measured.

| | Zeta potential in mV | |
| --- | --- | --- |
| | No DNA | DNA added |
| pH = 4.2 | +27.1 | −45.7 |
| pH = 7.5 | −6.3 | −39.6 |

EXAMPLE 8

Fusion Properties

Liposomes having the following compositions are produced as in Example 1 (all figures in mole-%)
A) POPC 60 His-Chol 40
X) POPC 100
Y) POPC 60 DPPG 40

The optionally cationic liposomes A are incubated with the neutral liposomes X or with the anionic liposomes Y in buffer (10 mM HEPES, 10 mM potassium acetate, pH 4.2 or 7.5). Possible fusion of liposomes is analyzed using size measurement by means of dynamic light scattering.

| | Liposome 1 | |
| --- | --- | --- |
| | X | Y |
| | Liposome 2 | |
| | A | A |
| pH 4.2 | 181.6 nm | 1689.3 nm |
| pH 7.5 | 191.8 nm | 250.0 nm |

The initial values of the liposomes were 161.8 nm at pH 4.2 and 165.9 nm at pH 7.5
X) 199.2 nm
Y) 183.2 nm The size of the YA pair of complementary charge is clearly different from the size of the mixed suspensions including the neutral liposome XA. The degree of interaction is determined by the charge level of the optionally cationic liposomes. Fusion to form larger units does not depend on the fusogenic PE lipid.

EXAMPLE 9

Permeability to Macromolecules

15 µmol of DOPE and 10 µmol of His-Chol are dissolved in isopropanol, and the solvent is removed under vacuum. The dried lipid film is added with 2.5 ml of a solution of proteinase K in buffer (1 mg/ml proteinase K, 10 mM potassium acetate, 10 mM HEPES, 150 mM NaCl, pH 4.2). Following hydration of the film, the liposomes having formed are extruded through a 400 nm membrane. Non-entrapped proteinase is removed by flotation of the liposomes in a sucrose gradient.

The liposomes thus produced are incubated with 7.5 ml of buffer at pH 4.2 and pH 7.2 (buffer as above, initial pH 4.2 and 8.0). Following incubation, the liberated proteinase K is separated by ultrafiltration using a 0.1 µm membrane. The liposomes remaining in the filter are then treated with 7.5 ml of a solution of Triton X-100 in buffer (as above, pH 8.0).

All of the filtrates are tested for presence of proteinase K. To this end, a solution of azocasein (6 mg/ml azocasein in 1 M urea, 200 mM Tris sulfate, pH 8.5) is used. 500 µl of this solution is mixed with 100 µl of filtrate or buffer and incubated for 30 minutes at 37° C. The reaction is terminated by addition of 10% trichloroacetic acid. Precipitated proteins are removed by centrifugation. The coloration in the supernatant is measured at 390 nm.

| pH Incubation | Triton X-100 | Absorption at 390 nm - blank |
| --- | --- | --- |
| 4.2 | − | 0.0165 |
| 4.2 | + | 0.1731 |
| 7.2 | − | 0.1354 |
| 7.2 | + | 0.0260 |

When incubating the liposomes at a pH value of 4.2, no or only a small amount of proteinase K is liberated. The enzyme is liberated only after dissolving the liposomes with Triton X-100.

When incubating the liposomes at a pH value of 7.2, a major amount of the enzyme is liberated even without addition of Triton and will be found in the first filtrate. Addition of Triton then is barely capable of leaching further enzyme from the liposomes.

EXAMPLE 10

Cytotoxicity

The toxic effect of the substances was investigated using the MTT test. To this end, HeLa cells were seeded at a density of $2\times10^4$ cells per cavity of a 96-well titer plate and cultured for two days. Liposomes of varying composition (see Table) were added to the cells at a concentration of 0.5 mM and incubated with these cells for 24 hours. Subsequently, the MTT test was performed.

| Liposome | Viability (MTT) | Notes |
|---|---|---|
| — | 100% | Cells detaching |
| DOPE 60/DOTAP 40 | 82% | |
| DOPE 60/DC-Chol 40 | 57% | |
| DOPE 60/His-Chol 40 | 92% | |
| DOPE 60/Mo-Chol 40 | 103% | |
| POPC 60/His-Chol 40 | 90% | |

DOPE: Dioleoylphosphatidyl ethanolamine, 60 mole-% each time POPC: Palmitoyloleoylphosphatidyl choline, 60 mole-% each time DC-Chol: N,N-Dimethyl (2-aminoethyl) carbamoylcholesterol Even at high concentrations, the liposomes comprising the substances of the invention are well-tolerated by cells. Toxic effects are barely detectable. In contrast, well-known cationic lipids such as DC-Chol or DOTAP have a significant cytotoxic effect.

EXAMPLE 11

Stability in Serum

Carboxyfluoresceine-loaded liposomes having the compositions POPC/His-Chol 60:40, POPC/Mo-Chol 60:40, and POPC/DPPG 60:40 (all figures in mole-%) were produced in analogy to Example 5. For measurement, the liposomes were diluted to 0.1 mM in human serum and incubated at 37° C. Fluorescence was measured at specific intervals. Complete liberation was achieved by addition of Triton X-100 to the measuring buffer. The CF liberation data are summarized in the Table below. For comparison, the negatively charged POPC/DPPG liposomes virtually losing no CF during 4 hours are illustrated. POPC/His-Chol liposomes show high serum stability up to 2 hours, but lose some CF after 4 hours. POPC/Mo-Chol liposomes exhibit a somewhat higher permeability than POPC/His-Chol.

| | POPC/His-Chol | POPC/Mo-Chol | POPC/DPPG |
|---|---|---|---|
| 0 min | 0% | 0% | 0% |
| 30 min | 0% | 4% | 0% |
| 60 min | 2% | 5% | 1% |
| 120 min | 4% | 9% | 2% |
| 240 min | 19% | 16% | 2% |

EXAMPLE 12

Transfection into Cells

HeLa cells ($3\times10^5$) were placed in each cavity of a 6-well titer plate and cultured for three days. Liposomes having the same compositions as in Example 10 were produced in the presence of fluorescence-labelled dextran (TRITC dextran, 10 mg/ml in hydration buffer). Non-incorporated TRITC dextran was removed by gel filtration. The liposomes thus produced were added to the cells and incubated for 6 hours at 37° C. Subsequently, the cells were washed twice with buffer. Dextran uptake was monitored by microscopic imaging and quantified using fluorescence spectroscopy.

The results are summarized in the following Table and in FIG. 2.

| Liposome | TRITC dextran uptake in μg |
|---|---|
| - (TRITC dextran in buffer) | 0.1 |
| DOPE 60/DOTAP 40 | 1.5 |
| DOPE 60/DC-Chol 40 | 1.1 |
| DOPE 60/His-Chol 40 | 0.3 |
| DOPE 60/Mo-Chol 40 | 0.7 |
| POPC 60/His-Chol 40 | 0.4 |

The new compounds do not quite achieve the efficiency of the well-known cationic lipids DOTAP or DC-Chol. However, they are also capable of mediating the transfection of macromolecules into cells. It is to be expected that the efficiency can be increased substantially when using ligands for cell adhesion.

The invention of claimed is:

1. A sterol derivative according to general formula (1):

$$\text{cation-spacer 2-Y-spacer 1-X-sterol} \tag{1}$$

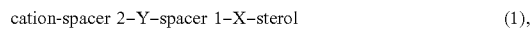

wherein;
said cation is a nitrogen base selected from the group consisting of piperazines, imidazoles, morpholines, purines, pyrimidines, and pyridines;
said spacers 1 and 2 are independently linear, or branched $C_{1-8}$ alkyl, and comprise 0-2 ethylenically unsaturated bonds;
said linking group X is selected from the group consisting of —(C=O)—O— and —(C=O)—NH—;
said linking group Y is selected from the group consisting of —O—(O=C)—, —NH—(O=C)—(C=O)—O—, and —(C=O)—NH—;
said sterol is selected from the group consisting of cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en-3β-ol, 7-hydroxycholesterol, epicholesterol, ergosterol, and dehydroergosterol; and
said sterol derivative has a pKa value of between about 3.5 and about 8.

2. The sterol derivative according to claim 1, wherein the sterol derivative has a pKa value of between about 4 and about 7.

3. A liposome comprising the sterol derivative of claim 1.

4. The liposome of claim 3, wherein said liposome comprises between about 5 mole-% and about 50 mole-% of sterol derivatives.

5. The liposome of claim 4, wherein said liposome comprises between about 5 mole % and about 40 mole-% of sterol derivatives.

6. The liposome of claim 5, wherein said liposome comprises between about 10 mole-% and about 30 mole-% of sterol derivatives.

7. The liposome of claim 3, wherein the liposome comprises one or more lipids secreted from the group consisting of phosphatidyl choline, phosphatidyl ethanolamine, and diacylglycerol.

8. The liposome of claim 7, wherein said liposome is neutral or negatively charged at a pH of from about 7.0 to about 7.8.

9. The liposome of claim 3, wherein said liposome has an average size of between about 50 and 1000 nm.

10. The liposome of claim 9, wherein said liposome has an average size of between about 50 and 300 nm.

11. The liposome of claim 10, wherein said liposome has an average size of between about 60 and 130 nm.

12. The liposome of claim 3, wherein said liposome further comprises an active substance.

13. The liposome claim 12, wherein said active substance is selected from the group consisting of a protein, peptide, a DNA, an RNA, an antisense nucleotide, a decoy nucleotide, and a mixture thereof.

14. The liposome of claim 12, wherein at least about 80% of said active substance is situated inside the liposome.

15. A method of loading the liposome of claim 12 with an active substance, said method comprising:
encapsulating said active substance in said liposome at a binding pH value; and removing unbound active substances at a second pH value.

16. A method of loading the liposome of claim 12 with an active substance, said method comprising:
permeabilizing said liposome by treatment at a pH value sufficient to enable loading of said active substance and sealing said liposome.

17. A method for tim transport and release of an active substance in a subject. said method comprising administering to said subject the liposome of claim 12.

18. The method of claim 17, wherein said administration is intravenous or peritoneal.

19. A transport and release system for the transport and release of an active substance in a subject, said system comprising the liposome of claim 12.

20. A depot formulation or circulative depot comprising the liposome of claim 12.

21. A nanocapsule prepared from the liposome of claim 3.

22. A vector for transfecting cells *in vivo, in vitro* or *ex vivo*, said vector comprising the liposome of claim 3 and a nucleic acid.

* * * * *